US011559891B2

(12) United States Patent
Tsuboi

(10) Patent No.: US 11,559,891 B2
(45) Date of Patent: Jan. 24, 2023

(54) ROBOT SYSTEM AND METHOD FOR CONTROLLING ROBOT SYSTEM

(71) Applicant: KAWASAKI JUKOGYO KABUSHIKI KAISHA, Kobe (JP)

(72) Inventor: Nobutaka Tsuboi, Kakogawa (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 269 days.

(21) Appl. No.: 16/626,177

(22) PCT Filed: Jun. 19, 2018

(86) PCT No.: PCT/JP2018/023280
§ 371 (c)(1),
(2) Date: Dec. 23, 2019

(87) PCT Pub. No.: WO2018/235812
PCT Pub. Date: Dec. 27, 2018

(65) Prior Publication Data
US 2020/0180154 A1   Jun. 11, 2020

(30) Foreign Application Priority Data
Jun. 21, 2017  (JP) .............................. JP2017-121331

(51) Int. Cl.
*B25J 9/16*  (2006.01)
*B25J 17/02*  (2006.01)
(Continued)

(52) U.S. Cl.
CPC .......... *B25J 9/1653* (2013.01); *B25J 9/1638* (2013.01); *B25J 9/1651* (2013.01); *B25J 17/02* (2013.01);
(Continued)

(58) Field of Classification Search
CPC ...... B25J 9/1694; B25J 9/0096; B25J 9/1628; B25J 9/1651; B25J 13/02; B25J 19/027;
(Continued)

(56) References Cited

U.S. PATENT DOCUMENTS

| 6,069,463 A | 5/2000 | Umeda et al. |
| 2007/0151389 A1* | 7/2007 | Prisco .................... B25J 9/1633 74/490.05 |

(Continued)

FOREIGN PATENT DOCUMENTS

| JP | H09-222910 A | 8/1997 |
| JP | 2011-136391 A | 7/2011 |

(Continued)

OTHER PUBLICATIONS

Iwasaki et al., "Modeling and Compensation for Angular Transmission Error of Harmonic Drive Gearings in High Precision Positioning," 2009 IEEE/ASME International Conference on Advanced Intelligent Mechatronics, 2009, pp. 662-667.

*Primary Examiner* — Abb Y Lin
*Assistant Examiner* — Dylan M Katz
(74) *Attorney, Agent, or Firm* — Oliff PLC

(57) ABSTRACT

A robot system has first and second joint control units that respectively calculate first and second current values to be supplied to first and second motors based on deviations between first and second operation targets for the motors that are input from a higher device and actual operation of output shafts of the motor, and control operation of the output shafts by supplying current to the motors based on the current values, and an error estimation unit estimating an error in operation of a second joint due to bending and/or twisting of a robot arm based on the first current value and the actual operation of the output shaft of the first motor, in which the second joint control unit calculates the second current value to control the rotation angle of the output shaft of the second (Continued)

motor in a manner compensating for an angle error of the second joint.

6 Claims, 5 Drawing Sheets

(51) Int. Cl.
    *G05B 19/23*      (2006.01)
    *A61B 34/30*      (2016.01)

(52) U.S. Cl.
    CPC ............ *G05B 19/231* (2013.01); *A61B 34/30* (2016.02); *G05B 2219/41398* (2013.01)

(58) Field of Classification Search
    CPC ...... B25J 15/0019; A61B 34/30; A61B 17/14; A61B 34/74; A61B 17/16; A61B 2034/101; A61B 2034/2055; A61B 2017/00367; A61B 17/1622; G05G 2009/04755

See application file for complete search history.

(56) References Cited

U.S. PATENT DOCUMENTS

| 2015/0039128 | A1 | | 2/2015 | Oaki |
| 2016/0221189 | A1 | * | 8/2016 | Nilsson ................. B25J 9/1653 |
| 2016/0297069 | A1 | * | 10/2016 | Negishi ................. B25J 9/1638 |
| 2017/0190049 | A1 | * | 7/2017 | Wada .................... B25J 9/1641 |

FOREIGN PATENT DOCUMENTS

| JP | 2011136391 A | * | 7/2011 |
| JP | 2012122509 A | * | 6/2012 |
| JP | 2014-136260 A | | 7/2014 |
| JP | 2015-030076 A | | 2/2015 |

* cited by examiner

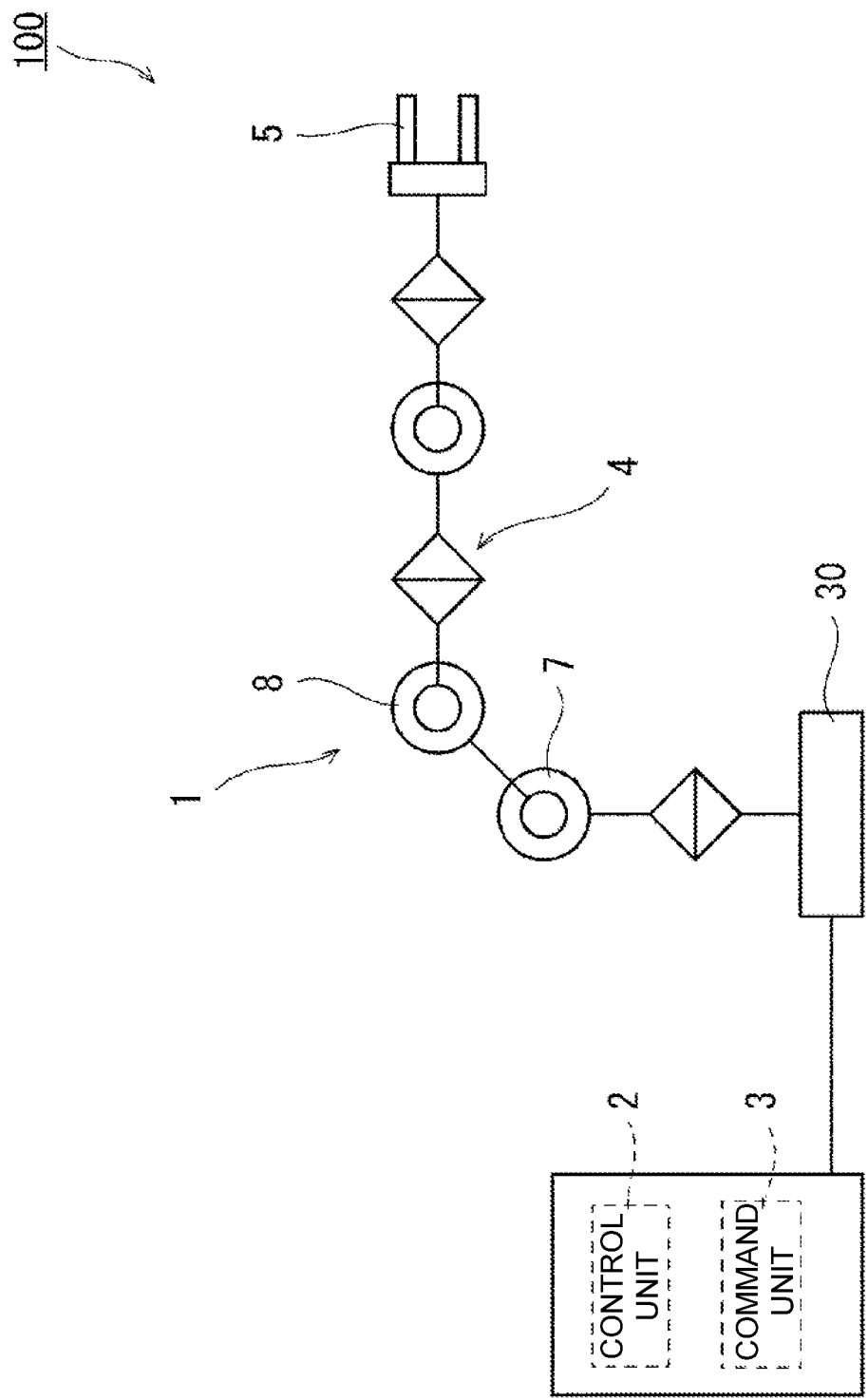
[Fig. 1]

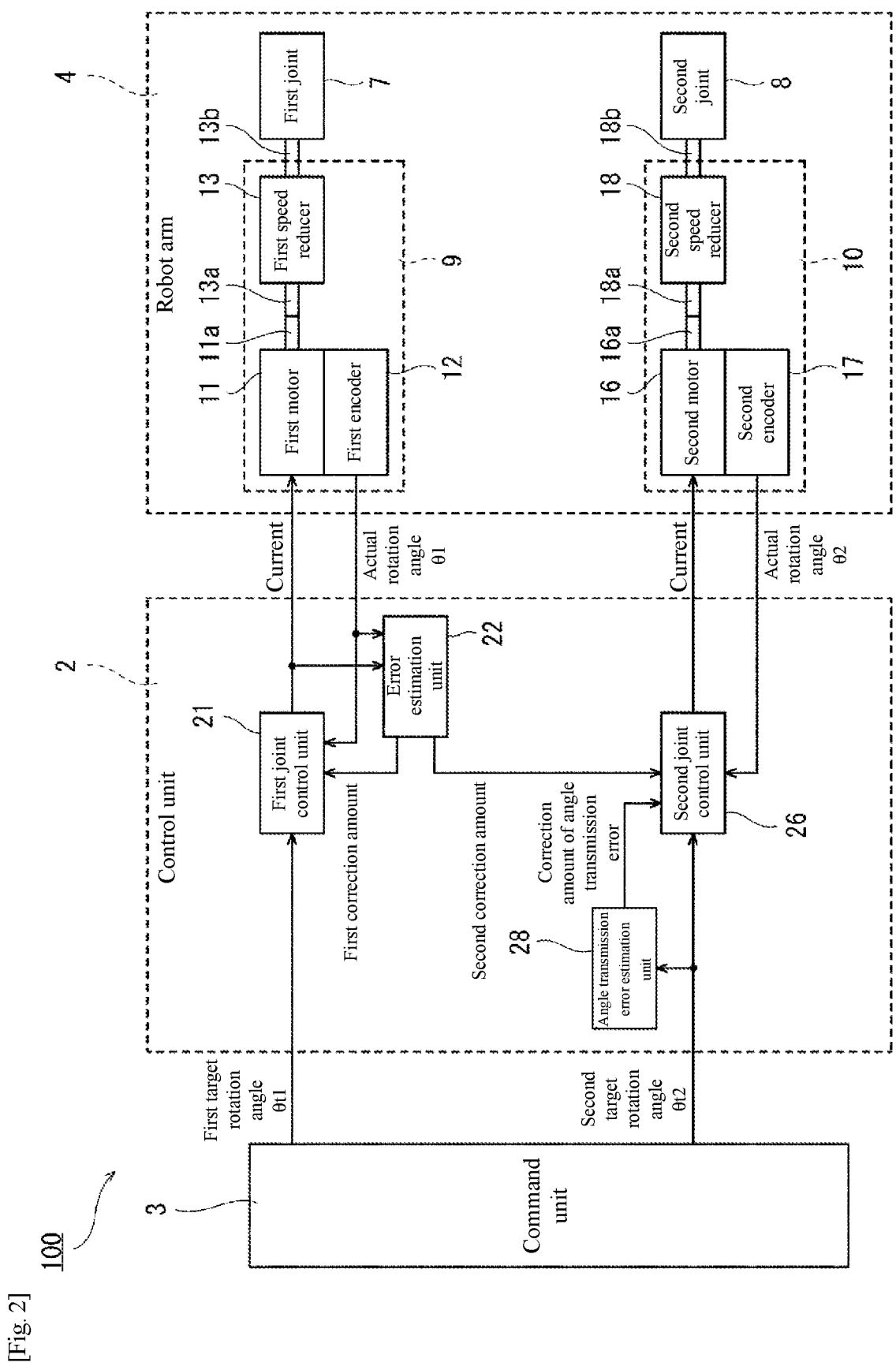
[Fig. 2]

[Fig. 3]
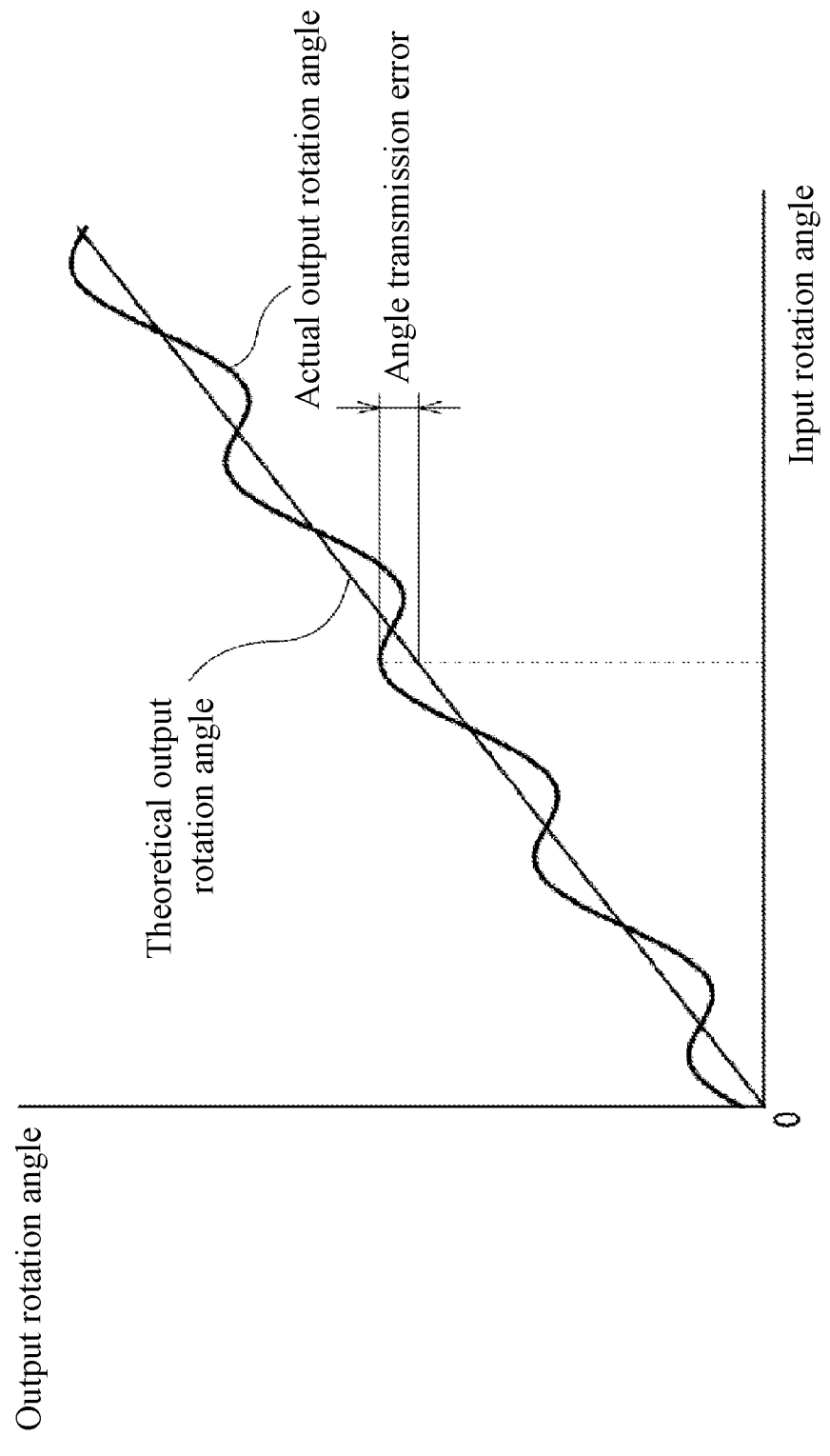

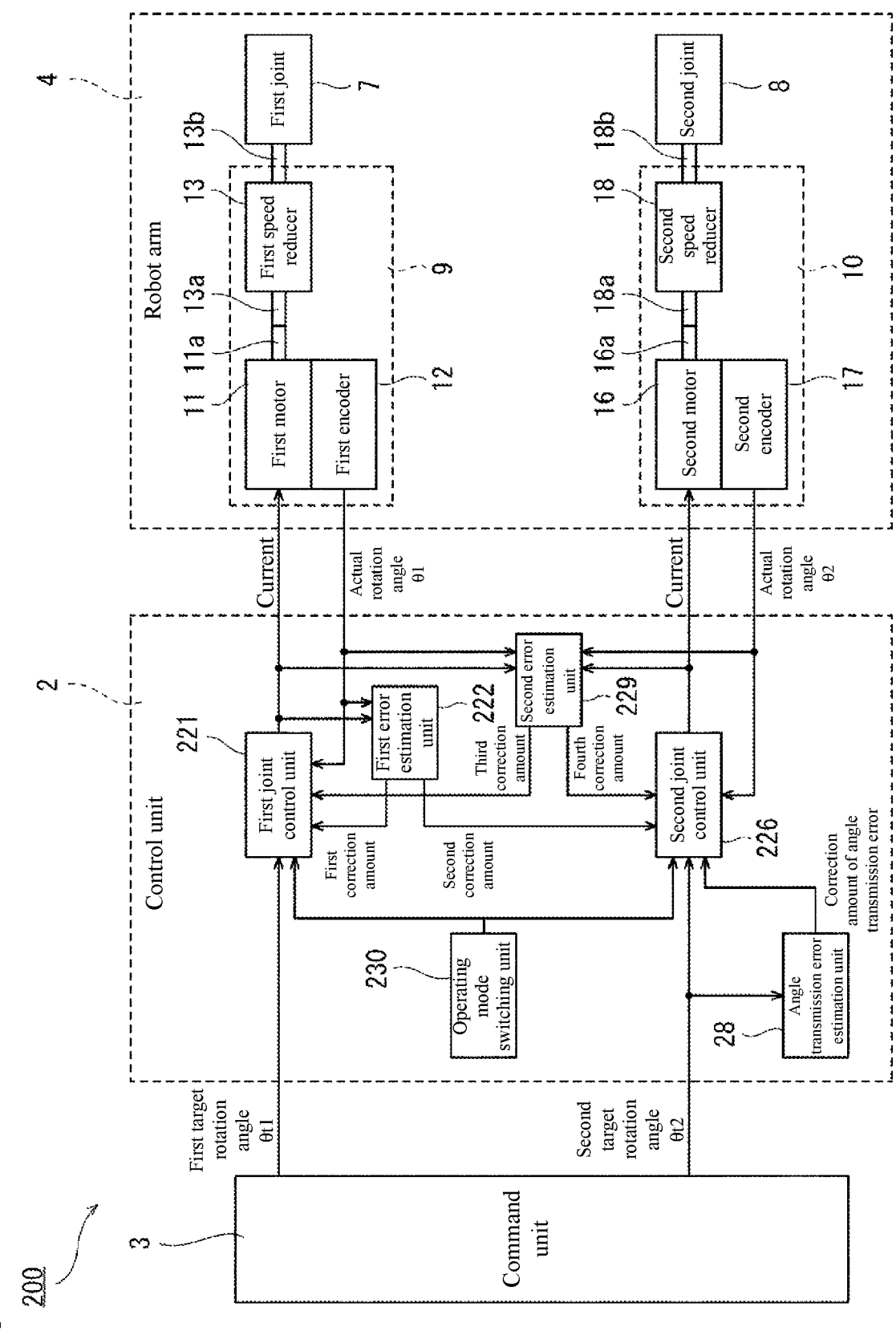
[Fig. 4]

[Fig. 5]
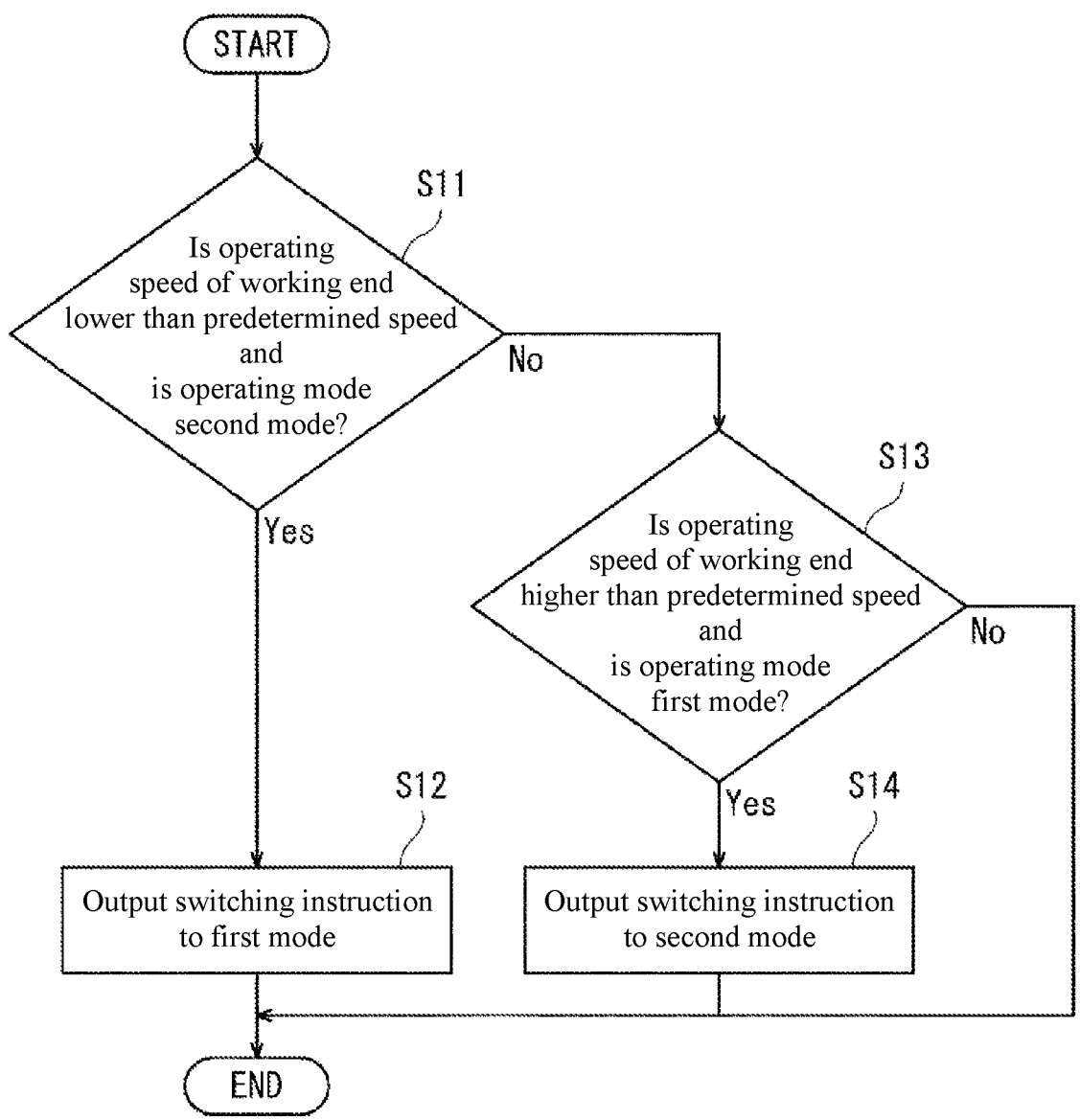

ROBOT SYSTEM AND METHOD FOR CONTROLLING ROBOT SYSTEM

TECHNICAL FIELD

The present invention relates to a robot system and a method for controlling the robot system.

BACKGROUND ART

Conventionally, there has been known a robot control device capable of enhancing a vibration suppressing effect at a distal end of a robot arm (see, for example, PTL 1).

This robot control device has an angular velocity control system that performs, for a control target that is a robot arm having an elastic mechanism, proportional integration control of an angular velocity of a motor and outputs a current command value to the motor, an observer that has a nonlinear dynamic model of the robot arm, receives the angular velocity of the motor and a current command value as inputs, and estimates an axial torsion angular velocity and an angular acceleration of a link, and a state feedback unit that calculates an axial torsion angular velocity from the difference between the angular velocity of the link estimated by the observer and the angular velocity of the motor and feeds back the axial torsion angular velocity to the angular velocity control system.

CITATION LIST

Patent Literature

PTL 1: JP 2015-30076 A

SUMMARY OF INVENTION

Technical Problem

However, since the robot control device described in PTL 1 estimates the axial torsion angular velocity of an estimation target joint based on the angular velocity of the motor included in the estimation target joint and the current command value for the motor, there have been cases where the axial torsion angular velocity cannot be estimated when the current command value for the motor includes any other compensation element.

Solution to Problem

In order to solve the above problems, a robot system according to an aspect of the present invention includes a robot arm that includes a plurality of joints including a first joint and a second joint, a first joint drive unit that has a first motor having an output shaft connected to the first joint to rotate the first joint, a first detection unit that obtains information on actual operation of the output shaft of the first motor, a first joint control unit that calculates a first current value to be supplied to the first motor based on a deviation between a first operation target for the first motor that is input from a higher device and the actual operation of the output shaft of the first motor, and controls operation of the output shaft of the first motor by supplying current to the first motor based on the first current value, a second joint drive unit that has a second motor having an output shaft connected to the second joint to rotate the second joint, a second detection unit that obtains information on actual operation of the output shaft of the second motor, a second joint control unit that calculates a second current value to be supplied to the second motor based on a deviation between a second operation target for the second motor that is input from the higher device and the actual operation of the output shaft of the second motor, and controls operation of the output shaft of the second motor by supplying current to the second motor based on the second current value, and an error estimation unit that estimates an error in operation of the second joint due to bending and/or twisting of the robot arm based on the first current value and the actual operation of the output shaft of the first motor, in which the second joint control unit calculates the second current value so as to control the operation of the output shaft of the second motor in a manner compensating for the error in operation of the second joint due to bending and/or twisting of the robot arm.

With this configuration, it is possible to prevent control to compensate for an error in operation of the second joint due to bending and/or twisting of the robot arm from interfering with other control. Thus, vibrations of the robot arm can be effectively suppressed, and trajectory accuracy of a working end of the robot arm can be improved.

Advantageous Effects of Invention

The present invention has an effect of improving trajectory accuracy of a working end of a robot arm.

BRIEF DESCRIPTION OF DRAWING

FIG. 1 is a diagram schematically illustrating a configuration example of a robot system according to Embodiment 1.

FIG. 2 is a block diagram schematically illustrating a configuration example of a control system of the robot system of FIG. 1.

FIG. 3 is an explanatory diagram of an angle transmission error.

FIG. 4 is a block diagram schematically illustrating a configuration example of a control system of a robot system according to Embodiment 2.

FIG. 5 is a flowchart illustrating an operation example of an operating mode switching unit of the robot system of FIG. 4.

DESCRIPTION OF EMBODIMENTS

A robot system according to an aspect includes a robot arm that includes a plurality of joints including a first joint and a second joint, a first joint drive unit that has a first motor having an output shaft connected to the first joint to rotate the first joint, a first detection unit that obtains information on actual operation of the output shaft of the first motor, a first joint control unit that calculates a first current value to be supplied to the first motor based on a deviation between a first operation target for the first motor that is input from a higher device and the actual operation of the output shaft of the first motor, and controls operation of the output shaft of the first motor by supplying current to the first motor based on the first current value, a second joint drive unit that has a second motor having an output shaft connected to the second joint to rotate the second joint, a second detection unit that obtains information on actual operation of the output shaft of the second motor, a second joint control unit that calculates a second current value to be supplied to the second motor based on a deviation between a second operation target for the second motor that is input from the higher device and the actual operation of the output shaft of the second motor, and controls operation of the output shaft of the second motor by supplying current to the second motor based on the second current value, and an error estimation unit that estimates an error in operation of the second joint due to bending and/or twisting of the robot arm based on the first current value and the actual operation of the output shaft of the first motor, in which the second joint control unit calculates the second current value so as to control the operation of the output shaft of the second motor in a manner compensating for the error in operation of the second joint due to bending and/or twisting of the robot arm.

With this configuration, it is possible to prevent control to compensate for an error in operation of the second joint due to bending and/or twisting of the robot arm from interfering with other control. Thus, vibrations of the robot arm can be effectively suppressed, and trajectory accuracy of a working end of the robot arm can be improved.

The information on the actual operation obtained by the first detection unit may be at least one of an angular position, an angular velocity, and an angular acceleration of the output shaft of the first motor, the first operation target may be at least one of a position command, a speed command, and an acceleration command for the first motor, the deviation between the first operation target and the actual operation of the output shaft of the first motor may be at least one of a position deviation, a speed deviation, and an acceleration deviation, the information on the actual operation obtained by the second detection unit may be at least one of an angular position, an angular velocity, and an angular acceleration of the output shaft of the second motor, the second operation target may be at least one of a position command, a speed command, and an acceleration command for the second motor, the deviation between the second operation target and the actual operation of the output shaft of the second motor may be at least one of a position deviation, a speed deviation, and an acceleration deviation, and the error in operation of the second joint due to bending and/or twisting of the robot arm may be at least one of an angle error, an angular velocity error, and an angular acceleration error.

With this configuration, it is possible to appropriately compensate for an error in operation of the second joint due to bending and/or twisting of the robot arm.

The error estimation unit may estimate the error in operation of the second joint due to bending and/or twisting of the robot arm based on one natural frequency with a small natural frequency among a plurality of natural frequencies of coupled vibrations of a system including the first joint and the second joint due to bending and/or twisting of the robot arm.

With this configuration, it is possible to appropriately suppress vibrations of the robot arm caused by bending and/or twisting of the robot arm.

The second joint drive unit may further include a speed reducer that has an input shaft connected to the output shaft of the second motor and an output shaft connected to the second joint, the second motor rotates the second joint via the speed reducer, and the robot system further comprises an angle transmission error estimation unit that estimates an angle transmission error between the rotation angle of the output shaft of the second motor and the rotation angle of the output shaft of the speed reducer, and the second joint control unit may calculate the second current value so as to control the operation of the output shaft of the second motor in a manner compensating for the angle transmission error and the error in operation of the second joint due to bending and/or twisting of the robot arm.

With this configuration, it is possible to prevent interference between compensation for an angle transmission error and compensation for an error in operation due to the bending and/or twisting of the robot arm. Thus, both the compensation for an angle transmission error and the compensation for an error in operation can be used together, and vibration of the robot arm can be effectively suppressed.

The error estimation unit may have a first error estimation unit that estimates the error in operation of the second joint due to bending and/or twisting of the robot arm based on the first current value and the actual operation of the output shaft of the first motor, and a second error estimation unit that estimates the error in operation of the second joint due to bending and/or twisting of the robot arm based on the second current value and the actual operation of the output shaft of the second motor, in which the second joint control unit may have a first mode in which the second current value is calculated so as to control operation of the output shaft of the second motor in a manner compensating for the angle transmission error and the error in operation of the second joint due to bending and/or twisting of the robot arm estimated by the first error estimation unit, and a second mode in which the second current value is calculated so as to control operation of the output shaft of the second motor in a manner compensating for the error in operation of the second joint due to bending and/or twisting of the robot arm estimated by the second error estimation unit, and the robot system may further include an operating mode switching unit that instructs the second joint control unit to switch between the first mode and the second mode.

With this configuration, it is possible to appropriately suppress vibrations of the robot arm by appropriately switching the mode according to conditions.

The operating mode switching unit may switch to the first mode when an operating speed of a working end of the robot arm becomes a predetermined speed or lower.

With this configuration, it is possible to reduce influence of the angle transmission error when performing work requiring accuracy.

A method for controlling a robot system according to an aspect is a method for controlling a robot system including a robot arm that includes a plurality of joints including a first joint and a second joint, a first joint drive unit that has a first motor having an output shaft connected to the first joint to rotate the first joint, a first detection unit that obtains information on actual operation of the output shaft of the first motor, a first joint control unit that controls operation of the output shaft of the first motor, a second joint drive unit that has a second motor having an output shaft connected to the second joint to rotate the second joint, a second detection unit that detects an event for detecting an actual rotation angle of the output shaft of the second motor, and a second joint control unit that controls operation of the output shaft of the second motor, the method including the steps of calculating a first current value to be supplied to the first motor based on a deviation between a first operation target for the first motor that is input from a higher device and the actual operation of the output shaft of the first motor, estimating an error in operation of the second joint due to bending and/or twisting of the robot arm based on the first current value and the actual operation of the output shaft of the first motor, calculating a second current value to be supplied to the second motor based on a deviation between a second operation target for the second motor that is input from the higher device and the actual operation of the output shaft of the second motor, and calculating the second current value so as to control a rotation angle of the output shaft of the second motor in a manner compensating for an error in operation of the second joint, and supplying the second motor with current based on the second current value.

With this configuration, it is possible to prevent control to compensate for an error in operation of the second joint due to bending and/or twisting of the robot arm from interfering with other control. Thus, vibrations of the robot arm can be effectively suppressed, and trajectory accuracy of a working end of the robot arm can be improved.

Embodiments will be described below with reference to the drawings. Note that the present invention is not limited by the following embodiments. Further, in the following the same or corresponding elements will be denoted by the same reference signs throughout all the drawings, and a redundant description thereof will be omitted.

Embodiment 1

FIG. 1 is a diagram schematically illustrating a configuration example of a robot system 100 according to Embodiment 1.

As illustrated in FIG. 1, the robot system 100 includes a robot 1, a control unit 2, and a command unit 3.

[Configuration Example of Robot]

The robot 1 is an industrial robot (articulated robot) that is an articulated-type robot.

The robot 1 includes a base 30, a robot arm 4, and a hand 5. For example, the base 30 is fixed and placed on a floor surface and supports the robot arm 4 and the hand 5.

The robot arm 4 has a plurality of joints, and has a base end portion that is rotatably connected to the base 30. As the joints of the robot arm 4, a plurality of joints are disposed in series from the base end portion toward a distal end portion. Among the plurality of joints of the robot arm 4, one joint constitutes a first joint 7 (for example, a second axis), and another joint (for example, a third axis) different from the first joint 7 constitutes a second joint 8. The first joint 7 and the second joint 8 are configured so that the first joint 7 and the second joint 8 can be positioned in a posture to interfere with each other. The posture in which the first joint 7 and the second joint 8 interfere with each other refers to a posture in which a mutual inertia coefficient of an inertia matrix of a dynamic equation according to Equation (1) is large.

[Equation 1]

$$T = I\ddot{\phi} + H + G \quad (1)$$

where T is a vector $$\begin{bmatrix} \tau_1 \\ \tau_2 \end{bmatrix}$$

of torque that is applied to a base-end side joint and a distal-end side joint,
I is an inertia matrix $$\begin{bmatrix} I_{11} & I_{12} \\ I_{21} & I_{22} \end{bmatrix},$$

and $I_{12}$ and $I_{21}$ are mutual coefficients of inertia,
$\ddot{\phi}$ is a vector $$\begin{bmatrix} \ddot{\phi}_1 \\ \ddot{\phi}_2 \end{bmatrix}$$

of acceleration of the base-end side joint and the distal-end side joint,
H is Coriolis effect and centrifugal force, and
G is a gravity vector.

FIG. 2 is a block diagram schematically illustrating a configuration example of the control system of the robot system 100 of FIG. 1. Note that in FIG. 2, illustration of joints other than the first joint 7 and the second joint 8 are omitted.

As illustrated in FIG. 2, each joint of the robot arm 4 has a drive unit that drives the joint. Each drive unit includes a speed reducer that has an output shaft connected to the corresponding joint (rotation shaft), a servomotor as a drive source that has an output shaft connected to an input shaft of the speed reducer and rotates the corresponding joint via the speed reducer, and an encoder that detects a rotation angle of the output shaft of the servomotor. Thus, the output shaft of the servomotor is connected to the corresponding joint via the speed reducer. Further, the encoder also obtains information on actual operation of the output shaft of the servomotor. In the present embodiment, the encoder detects an angular position of the output shaft of the servomotor, and detects an actual rotation angle of the output shaft of the servomotor based on the angular position. In the present embodiment, the speed reducer of the second joint 8, that is, the second speed reducer 18 is, for example, a strain wave gear (Harmonic Drive (registered trademark)). Further, the speed reducer of the first joint 7 is, for example, a speed reducer with a less angle transmission error compared to the strain wave gear.

Hereinafter, for convenience of explanation, the servomotor, the speed reducer, and the encoder that drive the first joint 7 are referred to as a first motor 11, a first speed reducer 13, and a first encoder (first detection unit) 12, respectively, and these constitute a first joint drive unit 9. Further, the servomotor, the speed reducer, and the encoder that drive the second joint 8 are referred to as a second motor 16, a second speed reducer 18, and a second encoder (second detection unit) 17, respectively, and these constitute a second joint drive unit 10. Note that in the present embodiment, the rotation angle means an angular position but is not limited to this. The rotation angle may be a time differential value of the angular position, that is, an angular velocity or an angular acceleration.

The strain wave gear according to the second speed reducer 18 includes a circular spline, a flex spline, and a wave generator. The circular spline is a rigid internal gear, and is provided integrally with a housing for example. The flex spline is an external gear having flexibility and meshes with the circular spline. The flex spline has fewer teeth than the circular spline and is connected to the output shaft 18b. The wave generator is an elliptical cam that contacts an inside of the flex spline, and is connected to an input shaft 18a. Then, by rotating the input shaft, the wave generator moves a meshing position between the flex spline and the circular spline, and the flex spline rotates around a rotary axis according to the difference in the number of teeth between the circular spline and the flex spline, and the output shaft rotates. The strain wave gear has characteristics suitable for a speed reducer of a drive mechanism for a robot because of features such as small size and light weight, high reduction ratio, high torque capacity, and non-backlash.

Incidentally, as illustrated in FIG. 3, in a speed reducer such as a strain wave gear, an angle transmission error occurs, which is a difference between a theoretical output rotation angle obtained by multiplying an input rotation angle input to the reduction gear by a reduction ratio and an actual output rotation angle, due to a processing error or the like. This angle transmission error appears as a periodic change accompanying rotation of the input shaft. Such an angle transmission error ATE of the speed reducer output shaft can be approximately expressed by a model using a function according to the following equation (2).

[Equation 2]

$$ATE = A\sin(f\theta + \phi) \quad (2)$$

where A is amplitude of an angle transmission error model function, f is a frequency of the angle transmission error model function, (the number of waves of an angle transmission error per rotation of the output shaft of a motor)

θ is a rotation angle of the output shaft of a servo motor (input shaft of a speed reducer), and φ is a phase of the angle transmission error model function.

As illustrated in FIG. 1, the hand 5 is configured to be capable of performing a predetermined operation such as holding an article, and is attached to the distal end portion of the robot arm 4.

[Configuration Example of Control Unit]

As illustrated in FIG. 2, the control unit 2 controls each of the joints and includes, for example, an arithmetic unit such as a microcontroller, a CPU, an ASIC, or a programmable logic device (PLD) such as FPGA. The arithmetic unit may be constituted of an independent arithmetic unit that performs centralized control, or may be constituted of a plurality of arithmetic units that perform distributed control in cooperation with each other. The control unit 2 includes a first joint control unit 21, a second joint control unit 26, an error estimation unit 22, and an angle transmission error estimation unit 28. The first joint control unit 21, the second joint control unit 26, the error estimation unit 22, and the angle transmission error estimation unit 28 are functional blocks that are implemented by executing a predetermined control program by an arithmetic unit (not illustrated). Note that although the control unit 2 is constituted of an arithmetic unit separate from the command unit 3, the control unit 2 may be integrated with the command unit 3.

The first joint control unit 21 is a PI controller (proportional-integral controller), and calculates a first current value to be supplied to the first motor 11 based on a deviation between a first target rotation angle (first operation target) θt1 for the first motor 11 input from the command unit 3 (higher device) and an actual rotation angle θ1 of the output shaft 11a of the first motor 11 detected by the first encoder 12. Then, current is supplied to the first motor 11 based on the first current value, so as to control the rotation angle of the output shaft 11a of the first motor 11. That is, the first joint control unit 21 performs feedback control of the first motor 11 based on control to make the deviation between the first target rotation angle θt1 and the actual rotation angle θ1 become close to 0, and make the rotation angle of the output shaft 11a of the first motor 11 become close to the first target rotation angle θt1.

Further, in the process of calculating the first current value, the first joint control unit 21 calculates the first current value so as to control the rotation angle of the output shaft 11a of the first motor 11 in a manner compensating for an angle error of the first joint 7 due to bending and/or twisting of the robot arm 4 estimated by the error estimation unit 22 (details will be described later).

The second joint control unit 26 is a PI controller, and calculates a second current value to be supplied to the second motor 16 based on a deviation between a second target rotation angle (second operation target) θt2 for the second motor 16 input from the command unit 3 and an actual rotation angle θ2 of the output shaft 16a of the second motor 16 detected by the second encoder 17. Then, current is supplied to the second motor 16 based on the second current value, so as to control the rotation angle of the output shaft 16a of the second motor 16. That is, the second joint control unit 26 performs feedback control of the second motor 16 based on control to make the deviation between the second target rotation angle θt2 and the actual rotation angle θ2 become close to 0, and make the rotation angle of the output shaft 16a of the second motor 16 become close to the second target rotation angle θt2.

Further, in the process of calculating the second current value, the second joint control unit 26 calculates the second current value so as to control the rotation angle of the output shaft 16a of the second motor 16 in a manner compensating for an angle error of the second joint 8 due to bending and/or twisting of the robot arm 4 estimated by the error estimation unit 22 (details will be described later).

Furthermore, in the process of calculating the second current value, the second joint control unit 26 calculates the second current value so as to control the rotation angle of the output shaft 16a of the second motor 16 in a manner compensating for an angle transmission error between the rotation angle of the output shaft 16a of the second motor 16 and a rotation angle of the output shaft 18b of the second speed reducer 18 estimated by the angle transmission error estimation unit 28 (details will be described later).

Based on the first current value supplied to the first motor 11 and the actual rotation angle θ1 of the output shaft 11a of the first motor 11, the error estimation unit 22 estimates angle errors (motion errors) of the first joint 7 and the second joint 8 due to bending and/or twisting of the robot arm 4. Then, a first correction amount for correcting the first current value is calculated based on the estimated angle error of the first joint 7. Furthermore, a second correction amount for correcting the second current value is calculated based on the estimated angle error of the second joint 8.

That is, the error estimation unit 22 calculates angle errors of the first joint 7 and the second joint 8 due to bending and/or twisting of the robot arm 4 by using a model that receives the first current value and the actual rotation angle θ1 of the output shaft 11a of the first motor 11 as inputs, and outputs the angle errors of the first joint 7 and the second joint 8 due to bending and/or twisting of the robot arm 4.

Incidentally, when the robot arm 4 is bent or twisted and vibrates by operation of the robot arm 4, due to bending and/or twisting of the robot arm 4, a deviation occurs between a theoretical rotation angle of the output shaft 11a of the first motor 11 obtained from torque of the output shaft 11a when the first motor 11 is supplied with current based on the first current value and the actual rotation angle θ1 of the output shaft 11a of the first motor 11. Therefore, it is possible to estimate bending and/or twisting of the robot arm 4 based on the first current value and the actual rotation angle θ1 of the output shaft 11a of the first motor 11, and it is further possible to estimate an angle error of each joint due to bending and/or twisting of the robot arm 4.

In the present embodiment, a model is defined in advance that receives the first current value and the actual rotation angle θ1 of the output shaft 11a of the first motor 11 as inputs, and outputs angle errors of the first joint 7 and the second joint 8 due to bending and/or twisting of the robot arm 4, and using this model the error estimation unit 22 calculates angle errors of the first joint 7 and the second joint 8 due to bending and/or twisting of the robot arm 4 based on the first current value and the actual rotation angle θ1 of the output shaft 11a of the first motor 11.

As the model, for example, a model may be built that measures in advance a relationship among the first current value, the actual rotation angle θ1 of the output shaft 11a of the first motor 11, and angle errors of the first joint 7 and the second joint 8, receives the first current value and the actual rotation angle θ1 of the output shaft 11a of the first motor 11 as inputs from measurement values thereof, and estimates an angle error of the first joint 7 and an angle error of the second joint 8. Further, a dynamic model that estimates an angle error of the first joint 7 and an angle error of the second joint 8 from the relationship between torque of the output shaft 11a when the current corresponding to the first current value is supplied to the first motor 11 and the actual rotation angle θ1 of the output shaft 11a of the first motor 11 may be used to analytically calculate angle errors of the first joint 7 and the second joint 8.

Further, the error estimation unit 22 calculates a first correction amount for compensating for the estimated angle error of the first joint 7 and a second correction amount for compensating for the angle error of the second joint 8. The first correction amount and the second correction amount are input to the first joint control unit 21 and the second joint control unit 26, respectively.

Then, in the process of calculating the first current value based on the deviation between the first target rotation angle θt1 and the actual rotation angle θ1 of the output shaft 11a of the first motor 11, the first joint control unit 21 calculates the first current value in which the angle error of the first joint 7 estimated by the error estimation unit 22 is compensated for by adding the first correction amount.

Further, in the process of calculating the second current value based on the deviation between the second target rotation angle θt2 and the actual rotation angle θ2 of the output shaft 16a of the second motor 16, the second joint control unit 26 calculates the second current value in which the angle error of the second joint 8 estimated by the error estimation unit 22 is compensated for by adding the second correction amount.

Further, the error estimation unit 22 estimates an angle error of the second joint 8 based on an eigenvalue corresponding to one natural frequency with a small natural frequency among a plurality of natural frequencies of coupled vibrations of a system including the first joint 7 and the second joint 8 due to bending and/or twisting of the robot arm 4. In a case of the system constituted of the first joint 7 and the second joint 8, an angle error of the second joint 8 is estimated based on the eigenvalue corresponding to one natural frequency that is smaller out of two natural frequencies.

That is, vibrations of the first joint 7 and the second joint 8 are expressed as coupled vibrations with two degrees of freedom, and are expressed as a superposition of two natural vibration modes. A mode corresponding to one natural frequency with a small natural frequency out of natural frequencies of the two natural vibration modes is a first mode in which the first joint 7 and the second joint 8 vibrate in a same rotation direction as each other, and the other mode is a second mode in which the first joint 7 and the second joint 8 vibrate in opposite rotation directions to each other. In the present embodiment, since vibrations of the estimation target joint (second joint 8) are estimated only from information obtained from the joint (first joint 7) different from the estimation target joint, it is not possible to estimate vibrations for both vibration modes. Accordingly, trajectory accuracy of the working end (hand 5) of the robot arm 4 can be effectively improved by estimating an angle error of the second joint 8 based on a natural frequency corresponding to the first mode that has greater influence on decrease of trajectory accuracy of the working end (hand 5) of the robot arm 4, that is, one natural frequency with a small natural frequency among a plurality of natural frequencies of coupled vibrations of the system including the first joint 7 and the second joint 8.

The angle transmission error estimation unit 28 estimates an angle transmission error between the rotation angle of the output shaft 16a of the second motor 16 and the rotation angle of the output shaft 18b of the second speed reducer 18.

That is, the angle transmission error estimation unit 28 estimates an angle transmission error between the rotation angle of the output shaft 16a of the second motor 16 that is an input rotation angle with respect to the second speed reducer 18 and the rotation angle of the output shaft 18b of the second speed reducer 18 that is an output rotation angle of the second speed reducer 18 based on a periodic function obtained by modeling a periodic variation of the angle transmission error according to the above equation (2). Then, the angle transmission error estimation unit 28 calculates a correction amount to be added to the output shaft 16a of the second motor 16 in order to compensate for the angle transmission error (in order to cancel the angle transmission error).

For example, it has been found that a component having a frequency f related to 2 has a particularly large influence on the angle transmission error of the strain wave gear. Therefore, the frequency f of the second speed reducer 18 constituted of the strain wave gear may be defined as 2, and the correction amount may be calculated based on the above equation (1) using a separately identified amplitude A and phase φ corresponding to the frequency f. Thus, the angle transmission error estimation unit 28 estimates the angle transmission error based on the second target rotation angle θt2, and calculates a correction amount for compensating for an angle transmission error of the second joint 8.

Then, in the process of calculating the second current value based on the deviation between the second target rotation angle θt2 and the actual rotation angle θ2 of the output shaft 16a of the second motor 16, the second joint control unit 26 calculates the second current value in which the angle error of the second joint 8 estimated by the error estimation unit 22 and the angle transmission error of the second joint 8 estimated by the angle transmission error estimation unit 28 are compensated for by adding a correction amount for compensating for the angle transmission error of the second joint 8 estimated by the angle transmission error estimation unit 28. In this manner, the second joint control unit 26 compensates for the angle transmission error by feedforward control.

Incidentally, by the angle transmission error estimation unit 28 adding the correction amount for compensating for the angle transmission error of the second joint 8, a change in the second current value is one that combines a change due to compensation for the angle transmission error and a change due to bending and/or twisting of the robot arm 4. When it is attempted to estimate an angle error of the second joint 8 due to bending and/or twisting of the robot arm 4 based on the second current value, a compensation component for the angle transmission error included in the second current value and a component related to a change of the second current value due to bending and/or twisting of the robot arm 4 cannot be discriminated, and an error may occur in estimation of an angle error of the second joint 8.

However, in the present embodiment, since the error estimation unit 22 is configured to estimate an angle error of the second joint based on the first current value of the first joint 7 that is a joint different from the second joint 8 and does not include a compensation component for the angle transmission error, it is possible to prevent that compensation for the angle transmission error with respect to the second joint 8 interferes with estimation of an angle error of the second joint 8 due to bending and/or twisting of the robot arm 4, an error occurs in estimation of an angle error of the second joint 8, and suppression of vibrations of the robot arm 4 fails. Thus, compensation for the angle transmission error of the second joint 8 and compensation for the angle error due to bending and/or twisting of the robot arm 4 can be used together, and trajectory accuracy of the robot arm 4 can be further improved.

Thus, it is configured to perform compensation for the angle transmission error of the second joint 8 by feedforward control, and compensation for an angle error of the second joint 8 due to bending and/or twisting of the robot arm 4 by feedback control.

The command unit 3 generates a position command for each joint, that is, a target rotation angle of each joint, based on the operation program and outputs the position command. The target rotation angle of each joint includes a first target rotation angle θt1 for the first motor 11 and a second target rotation angle θt2 for the second motor 16. The output target rotation angle is input to a joint control unit including the first joint control unit 21 and the second joint control unit 26.

As described above, in the robot system 100, the error estimation unit 22 estimates an angle error of a joint due to bending and/or twisting of the robot arm 4, and the first joint control unit 21 and the second joint control unit 26 calculate a current value in which the angle error is compensated for, and thus trajectory accuracy of the working end of the robot arm 4 can be improved.

Further, in the robot system 100, since the error estimation unit 22 calculates an angle error of the second joint 8 from the first current value for the first motor 11 included in the first joint 7 and the actual rotation angle θ1 of the output shaft 11a of the first motor 11, compensation for the angle transmission error with respect to the second joint 8 can be prevented from interfering with estimation of an angle error of the second joint 8 due to bending and/or twisting of the robot arm 4, compensation for the angle transmission error of the second joint 8 and compensation for an angle error due to bending and/or twisting of the robot arm 4 can be used together, and trajectory accuracy of the robot arm 4 can be further improved.

Embodiment 2

A configuration and operation of Embodiment 2 will be described below, focusing on differences from Embodiment 1.

FIG. 4 is a block diagram schematically illustrating a configuration example of a control system of a robot system 200 according to Embodiment 2.

In Embodiment 1, the control unit 2 of the robot system 100 includes the first joint control unit 21, the second joint control unit 26, and the error estimation unit 22. On the other hand, in the present embodiment, the robot system 200 includes a first joint control unit 221, a second joint control unit 226, a first error estimation unit 222, a second error estimation unit 229, and an operating mode switching unit 230. Since the first error estimation unit 222 is configured similarly to the error estimation unit 22 according to above Embodiment 1, a detailed description thereof will be omitted.

The second error estimation unit 229 estimates an angle error of the first joint 7 due to bending and/or twisting of the robot arm 4 based on a first current value supplied to the first motor 11 and an actual rotation angle θ1 of the output shaft 11a of the first motor 11. Then, a third correction amount for correcting the first current value is calculated based on the estimated angle error of the first joint 7. Further, the second error estimation unit 229 estimates an angle error of the second joint 8 due to bending and/or twisting of the robot arm 4 based on a second current value supplied to the second motor 16 and an actual rotation angle θ2 of the second motor 16. Then, a fourth correction amount for correcting the second current value is calculated based on the estimated angle error of the second joint 8. The third correction amount and the fourth correction amount are input to the first joint control unit 221 and the second joint control unit 226, respectively.

The operating mode switching unit 230 generates a switching command between a first mode and a second mode, which will be described later, and the generated switching command is input to the first joint control unit 221 and the second joint control unit 226.

Then, the first joint control unit 221 has a first mode and a second mode. In the first mode, the first joint control unit 221 calculates the first current value so as to control a rotation angle of the output shaft 11a of the first motor 11 in a manner compensating for the angle error of the first joint 7 estimated by the first error estimation unit 222. That is, in the first mode, in the process of calculating the first current value based on a deviation between a first target rotation angle θt1 and the actual rotation angle θ1 of the output shaft 11a of the first motor 11, the first joint control unit 221 calculates the first current value in which the angle error of the first joint 7 estimated by the first error estimation unit 222 is compensated for by adding the first correction amount. Further, in the second mode, the first joint control unit 221 calculates the first current value so as to control the rotation angle of the output shaft 11a of the first motor 11 in a manner compensating for the angle error of the first joint 7 estimated by the second error estimation unit 229. That is, in the second mode, in the process of calculating the first current value based on the deviation between the first target rotation angle θt1 and the actual rotation angle θ1 of the output shaft 11a of the first motor 11, the first joint control unit 221 calculates the first current value in which the angle error of the first joint 7 estimated by the second error estimation unit 229 is compensated for by adding the third correction amount.

Further, the second joint control unit 226 has two operating modes, a first mode and a second mode. In the first mode, the second joint control unit 226 calculates the second current value so as to control the rotation angle of the output shaft 16a of the second motor 16 in a manner compensating for the angle transmission error and the angle error of the second joint 8 estimated by the first error estimation unit 222. That is, in the first mode, in the process of calculating the second current value based on the deviation between a second target rotation angle θt2 and the actual rotation angle θ2 of the output shaft 16a of the second motor 16, the second joint control unit 226 calculates the second current value in a manner compensating for the angle transmission error and the angle error of the second joint 8 estimated by the first error estimation unit 222 by adding the correction amount of the angle transmission error and the second correction amount. Further, in the second mode, the second joint control unit 226 calculates the second current value so as to control the rotation angle of the output shaft 16a of the second motor 16 in a manner compensating for the angle error of the second joint 8 estimated by the second error estimation unit 229. That is, in the second mode, in the process of calculating the second current value based on the deviation between the second target rotation angle θt2 and the actual rotation angle θ2 of the output shaft 16a of the second motor 16, the second joint control unit 226 calculates the second current value in which the angle error of the second joint 8 estimated by the second error estimation unit 229 is compensated for by adding the fourth correction amount.

Specifically, for the second joint 8, the first mode is a mode for performing processing similar to operation processing of the error estimation unit 22 in above Embodiment 1, and is a mode in which the second current value is calculated so as to control the rotation angle of the output shaft 16a of the second motor 16 in a manner compensating for the angle transmission error and compensating for the angle error of the second joint 8 calculated by the first error estimation unit 222, to thereby control operation of the second motor 16. On the other hand, the second mode is a mode in which the second current value is calculated so as to control the rotation angle of the output shaft 16a of the second motor 16 in a manner compensating for the angle error of the second joint 8 calculated by the second error estimation unit 229 without compensating for the angle transmission error, to thereby control operation of the second motor 16.

FIG. 5 is a flowchart illustrating an operation example of the operating mode switching unit 230.

The operating mode switching unit 230 instructs the first joint control unit 221 and the second joint control unit 226 to switch between the first mode and the second mode. Then, the operating mode switching unit 230 is configured to switch to the first mode when the operating speed of the working end (hand 5) of the robot arm 4 becomes a predetermined speed or less. In the present embodiment, as illustrated in FIG. 5, the operating mode switching unit 230 determines whether or not it is a state that the operating speed of the working end of the robot arm 4 is lower than a predetermined speed and the second mode is selected as the operating mode (step S11). When the operating mode switching unit 230 determines that it is a state that the operating speed of the working end of the robot arm 4 is lower than the predetermined speed and the second mode is selected as the operating mode (Yes in step S11), a switching command for switching the operating mode to the first mode is generated (step S12). Then, the operating mode switching unit 230 ends the process. Thus, when work that requires high accuracy such as arc welding is carried out, not only compensation for angle errors due to bending and/or twisting of the robot arm 4, but also compensation for angle transmission errors can be used together, and trajectory accuracy can be improved.

On the other hand, when the operating mode switching unit 230 determines that it is a state that the operating speed of the working end of the robot arm 4 is higher than the predetermined speed, or the first mode is selected as the operating mode (No in step S11), next, the operating mode switching unit 230 determines whether or not it is a state that the operating speed of the working end of the robot arm 4 is higher than the predetermined speed and the first mode is selected as the operating mode (step S13). Then, when the operating mode switching unit 230 determines that it is a state that the operating speed of the working end of the robot arm 4 is higher than the predetermined speed and the first mode is selected as the operating mode (Yes in step S13), a switching command for switching the operating mode to the second mode is generated (step S13). Then, the operating mode switching unit 230 ends the process. Thus, robustness can be enhanced when quick work is performed in which a decrease in trajectory accuracy due to the angle transmission error is not a problem.

On the other hand, when the operating mode switching unit 230 determines that it is a state that the operating speed of the working end of the robot arm 4 is lower than the predetermined speed, or the second mode is selected as the operating mode (No in step S13), the operating mode switching unit 230 ends the process. Then, the operating mode switching unit 230 repeatedly executes the above process at a predetermined cycle time. The other configuration is similar to that of above Embodiment 1, and thus a detailed description thereof will be omitted.

From the above description, many improvements and other embodiments of the present invention will be apparent to those skilled in the art. Therefore, the above description should be construed as exemplary only, and is provided for the purpose of teaching those skilled in the art the best mode for carrying out the present invention. Structural and/or functional details thereof may be substantially changed without departing from the spirit of the present invention.

REFERENCE SIGNS LIST 1 robot
2 control unit
3 command unit
4 robot arm
7 first joint
19
8 second joint
9 first joint drive unit
10 second joint drive unit
11 first motor
11a output shaft (of the first motor)
12 first encoder
13 first speed reducer
13a input shaft (of the first speed reducer)
13b output shaft (of the first speed reducer)
16 second motor
16a output shaft (of the second motor)
17 second encoder
18 second speed reducer
18a input shaft of (the second speed reducer)
18b output shaft (of the second speed reducer)
21 first joint control unit
22 first angle error estimation unit
26 second joint control unit
27 second angle error estimation unit
28 angle transmission error estimation unit
100 robot system

The invention claimed is:
1. A robot system comprising:
a robot arm that includes a plurality of joints including a first joint and a second joint;
a first joint drive unit that has a first motor having an output shaft connected to the first joint to rotate the first joint;
a first sensor that obtains information on actual operation of the output shaft of the first motor;

circuitry that calculates a first current value to be supplied to the first motor based on a deviation between a first operation target for the first motor that is input from a higher device and the actual operation of the output shaft of the first motor, and controls operation of the output shaft of the first motor by supplying current to the first motor based on the first current value;
a second joint drive unit that has a second motor having an output shaft connected to the second joint to rotate the second joint; and
a second sensor that obtains information on actual operation of the output shaft of the second motor, wherein
the circuitry calculates a second current value to be supplied to the second motor based on a deviation between a second operation target for the second motor that is input from the higher device and the actual operation of the output shaft of the second motor, and controls operation of the output shaft of the second motor by supplying current to the second motor based on the second current value,
the circuitry estimates an error in operation of the second joint due to bending and/or twisting of the robot arm based on the first current value, the actual operation of the output shaft of the first motor, and the smallest natural frequency among a plurality of natural frequencies of coupled vibrations of a system including the first joint and the second joint due to bending and/or twisting of the robot arm, and
the circuitry calculates the second current value so as to control the operation of the output shaft of the second motor in a manner compensating for the error in operation of the second joint due to bending and/or twisting of the robot arm.

2. The robot system according to claim 1, wherein
the information on the actual operation obtained by the first sensor is at least one of an angular position, an angular velocity, and an angular acceleration of the output shaft of the first motor,
the first operation target is at least one of a position command, a speed command, and an acceleration command for the first motor,
the deviation between the first operation target and the actual operation of the output shaft of the first motor is at least one of a position deviation, a speed deviation, and an acceleration deviation,
the information on the actual operation obtained by the second sensor is at least one of an angular position, an angular velocity, and an angular acceleration of the output shaft of the second motor,
the second operation target is at least one of a position command, a speed command, and an acceleration command for the second motor,
the deviation between the second operation target and the actual operation of the output shaft of the second motor is at least one of a position deviation, a speed deviation, and an acceleration deviation, and
the error in operation of the second joint due to bending and/or twisting of the robot arm is at least one of an angle error, an angular velocity error, and an angular acceleration error.

3. The robot system according to claim 1, wherein
the second joint drive unit further includes a speed reducer that has an input shaft connected to the output shaft of the second motor and an output shaft connected to the second joint,
the second motor rotates the second joint via the speed reducer,
the circuitry estimates an angle transmission error between a rotation angle of the output shaft of the second motor and a rotation angle of the output shaft of the speed reducer, and
the circuitry calculates the second current value so as to control the operation of the output shaft of the second motor in a manner compensating for the angle transmission error and the error in operation of the second joint due to bending and/or twisting of the robot arm.

4. The robot system according to claim 3, wherein
the circuitry is configured to estimate the error in operation of the second joint due to bending and/or twisting of the robot arm based on the first current value and the actual operation of the output shaft of the first motor, and is configured to estimate the error in operation of the second joint due to bending and/or twisting of the robot arm based on the second current value and the actual operation of the output shaft of the second motor,
the circuitry has a first mode in which the second current value is calculated so as to control the operation of the output shaft of the second motor in a manner compensating for the angle transmission error and the error in operation of the second joint due to bending and/or twisting of the robot arm estimated based on the first current value and the actual operation of the output shaft of the first motor, and a second mode in which the second current value is calculated so as to control the operation of the output shaft of the second motor in a manner compensating for the error in operation of the second joint due to bending and/or twisting of the robot arm estimated based on the second current value and the actual operation of the output shaft of the second motor, and
the circuitry is configured to switch between the first mode and the second mode.

5. The robot system according to claim 4, wherein the circuitry switches to the first mode when an operating speed of a working end of the robot arm becomes a predetermined speed or lower.

6. A method for controlling a robot system including:
a robot arm that includes a plurality of joints including a first joint and a second joint;
a first joint drive unit that has a first motor having an output shaft connected to the first joint to rotate the first joint;
a first sensor that obtains information on actual operation of the output shaft of the first motor;
circuitry that controls operation of the output shaft of the first motor;
a second joint drive unit that has a second motor having an output shaft connected to the second joint to rotate the second joint; and
a second sensor that detects an event for detecting an actual rotation angle of the output shaft of the second motor, wherein
the circuitry controls operation of the output shaft of the second motor,
the method comprising the steps of:
calculating a first current value to be supplied to the first motor based on a deviation between a first operation target for the first motor that is input from a higher device and the actual operation of the output shaft of the first motor;
estimating an error in operation of the second joint due to bending and/or twisting of the robot arm based on the first current value, the actual operation of the output shaft of the first motor, and the smallest natural frequency among a plurality of natural frequencies of coupled vibrations of a system including the first joint and the second joint due to bending and/or twisting of the robot arm;

calculating a second current value to be supplied to the second motor based on a deviation between a second operation target for the second motor that is input from the higher device and the actual operation of the output shaft of the second motor, and calculating the second current value so as to control a rotation angle of the output shaft of the second motor in a manner compensating for the error in operation of the second joint; and supplying the second motor with current based on the second current value.

* * * * *